(12) United States Patent
Lee

(10) Patent No.: US 7,622,472 B2
(45) Date of Patent: Nov. 24, 2009

(54) COMBINATION OF SRC KINASE INHIBITORS AND CHEMOTHERAPEUTIC AGENTS FOR THE TREATMENT OF PROLIFERATIVE DISEASES

(75) Inventor: Francis Y. Lee, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/047,623

(22) Filed: Mar. 13, 2008

(65) Prior Publication Data

US 2008/0153842 A1  Jun. 26, 2008

Related U.S. Application Data

(63) Continuation of application No. 10/886,955, filed on Jul. 8, 2004, now abandoned.

(60) Provisional application No. 60/485,779, filed on Jul. 9, 2003.

(51) Int. Cl.
*A61K 31/497* (2006.01)
*A61K 31/426* (2006.01)
*A61P 35/00* (2006.01)
*C07D 277/02* (2006.01)

(52) U.S. Cl. ............... 514/252.1; 514/365; 548/146

(58) Field of Classification Search ............... 514/252.1, 514/365; 548/146
See application file for complete search history.

(56) References Cited

U.S. PATENT DOCUMENTS

| 6,596,746 | B1 | 7/2003 | Das et al. |
| 2004/0024208 | A1 | 2/2004 | Das et al. |
| 2004/0054186 | A1 | 3/2004 | Das et al. |
| 2004/0057950 | A1 | 3/2004 | Waksal et al. |
| 2004/0073026 | A1 | 4/2004 | Das et al. |
| 2004/0077875 | A1 | 4/2004 | Das et al. |
| 2004/0209930 | A1 | 10/2004 | Carboni et al. |
| 2005/0215795 | A1 | 9/2005 | Chen et al. |

FOREIGN PATENT DOCUMENTS

| WO | WO00/62778 | 10/2000 |
| WO | WO03/013540 | 2/2003 |
| WO | WO2004/085388 | 10/2004 |
| WO | WO2005/076990 | 8/2005 |

OTHER PUBLICATIONS

Golas et al., "SKI-606, a 4-Anilino-3-quinolinecarbonitrile Dual Inhibitor of Src and Abl Kinases. Is a Potent Antiproliferative Agent Against Chronic Myelogenous Leukemia Cells in Culture and Causes Regression of K562 Xenografts in Nude Mice," *Cancer Research*, vol. 63, pp. 375-381, 2003.
Office Action and Response by applicant dated Apr. 8, 2005 for U.S. Appl. No. 10/378,373.
Office Action U.S. Appl. No. 11/271,626.

*Primary Examiner*—Michael G Hartley
*Assistant Examiner*—Shirley V Gembeh
(74) *Attorney, Agent, or Firm*—Mary K. VanAtten

(57) ABSTRACT

Compositions and methods are disclosed which are useful of the treatment and prevention of proliferative disorders.

7 Claims, 1 Drawing Sheet

COMBINATION OF SRC KINASE INHIBITORS AND CHEMOTHERAPEUTIC AGENTS FOR THE TREATMENT OF PROLIFERATIVE DISEASES

CROSS-REFERENCE TO RELATED APPLICATIONS

This application claims benefit to provisional application U.S. Ser. No. 60/485,779 filed Jul. 9, 2003. The entire teachings of the referenced application are incorporated herein by reference.

FIELD OF THE INVENTION

This invention relates to the fields of oncology and improved chemotherapy regimens.

BACKGROUND OF THE INVENTION

The disclosure of each literature article and published patent document referred to herein is incorporated by reference herein in its entirety.

The National Cancer Institute has estimated that in the United States alone, 1 in 3 people will be struck with cancer during their lifetime. Moreover, approximately 50% to 60% of people contracting cancer will eventually succumb to the disease. The widespread occurrence of this disease underscores the need for improved anticancer regimens for the treatment of malignancy.

Due to the wide variety of cancers presently observed, numerous anticancer agents have been developed to destroy cancer within the body. These compounds are administered to cancer patients with the objective of destroying or otherwise inhibiting the growth of malignant cells while leaving normal, healthy cells undisturbed. Anticancer agents have been classified based upon their mechanism of action.

One type of chemotherapeutic is referred to as a metal coordination complex. It is believed this type of chemotherapeutic forms predominantly inter-strand DNA cross links in the nuclei of cells, thereby preventing cellular replication. As a result, tumor growth is initially repressed, and then reversed. Another type of chemotherapeutic is referred to as an alkylating agent. These compounds function by inserting foreign compositions or molecules into the DNA of dividing cancer cells. As a result of these foreign moieties, the normal functions of cancer cells are disrupted and proliferation is prevented. Another type of chemotherapeutic is an antineoplastic agent. This type of agent prevents, kills, or blocks the growth and spread of cancer cells. Still other types of anticancer agents include nonsteroidal aromastase inhibitors, bifunctional alkylating agents, etc.

The present invention is directed to Src Kinase Inhibitors that act synergistically when used in combination with certain conventional chemotherapeutic agents.

SUMMARY OF THE INVENTION

The present invention provides a synergistic method for the treatment of anti-proliferative diseases, including cancer, which comprises administering to a mammalian specie in need thereof a synergistically, therapeutically effective amount of: (1) at least one anti-proliferative agent and/or one anti-proliferative cytotoxic agent and (2) a compound of formula I wherein

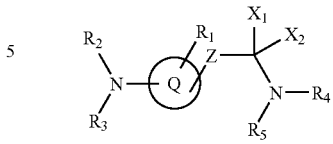

wherein Q, Z, N, $X_1$ and $X_2$ $R_1$, $R_2$, $R_3$, $R_4$, $R_4$, are defined below, or pharmaceutically acceptable salt or hydrate thereof.

A compound of Formula I is represented by 'N-(2-Chloro-6-methylphenyl)-2-[[6-[4-(2-hydroxyethyl)-1-piperazinyl]-2-methyl-4-pyrimidinyl]amino]-5-thiazolecarboxamide and pharmaceutically acceptable salts thereof.

Suitable anti-proliferative agents for use in the methods of the invention, include, without limitation, alkylating agents (including, without limitation, nitrogen mustards, ethylenimine derivatives, alkyl sulfonates, nitrosoureas and triazenes): Uracil mustard, Chlormethine, Cyclophosphamide (Cytoxan@), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide; antimetabolites (including, without limitation, folic acid antagonists, pyrimidine analogs, purine analogs and adenosine deaminase inhibitors), Methotrexate, 5-Fluorouracil, Floxuridine, Cytarabine, 6-Mercaptopurine, 6-Thioguanine, Fludarabine phosphate, Pentostatine, and Gemcitabine; natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as Taxol®), Mithramycin, Deoxyco-formycin, Mitomycin-C, L-Asparaginase, Interferons (especially IFN-a), Etoposide, and Teniposide; navelbene, CPT-11, anastrazole, letrazole, capecitabine, reloxafine, cyclophosphamide, ifosamide, and droloxafine and radiation.

The present invention further provides a pharmaceutical composition for the synergistic treatment of cancer which comprises at least one anti-proliferative agent, and a compound of Formulas I, and a pharmaceutically acceptable carrier.

In another embodiment of the invention the antiproliferative agent is administered simultaneous with or before or after the administration of a compound of Formulas I.

DETAILED DESCRIPTION OF THE INVENTION

Figure 1B:
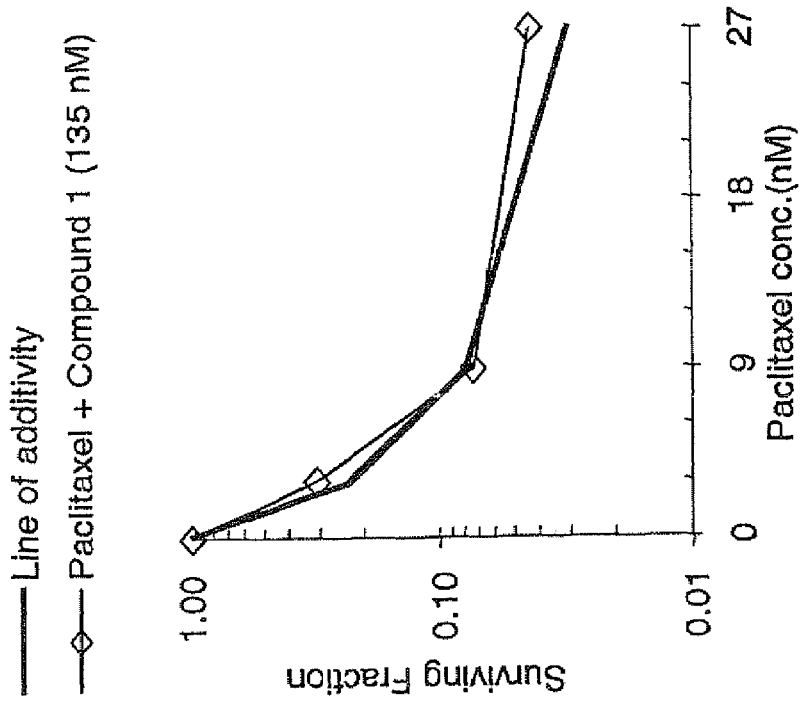
FIGS. 1A and 1B show the combination chemotherapy with compound 1 and paclitaxel in vivo (A) and in vitro (B) versus the PC3 human prostate carcinoma.

In accordance with the present invention, methods for the scheduled administration of Src Kinase inhibitors in synergistic combination(s) with at least one additional anti-neoplastic agent for the treatment and prevention of proliferative diseases are provided.

Thus, in an embodiment of the invention, the chemotherapeutic method of the invention comprises the administration of Src Kinase Inhibitors of Formulas I in combination with other anti-cancer agents. The Src Kinase Inhibitors disclosed herein, when used in combination with at least one other anti-cancer agent(s) demonstrate superior cytotoxic activity.

A Src Kinase Inhibitors for use in the methods of the invention is a compound of Formula I wherein

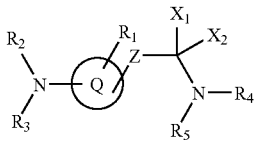

I where
Q is thiazole,
Z is a single bond;
$X_1$ and $X_2$ together form =O;
$R_1$ is
  (1) hydrogen or $R_6$,
    where $R_6$ is alkyl, alkenyl, alkynyl, cycloalkyl, cycloalkylalkyl, cycloalkenyl, cycloalkenylalkyl, aryl, aralkyl, heterocyclo, or heterocycloalkyl, each of which is unsubstituted or substituted with $Z_1$, $Z_2$ and one or more groups $Z_3$;
  (2) —OH or —$OR_6$;
  (3) —SH or —$SR_6$;
  (4) —$C(O)_2H$, —$C(O)_qR_6$, or —O—$C(O)_qR_6$, where q is 1 or 2;
  (5) —$SO_3H$ or —$S(O)_qR_6$,
  (6) halo;
  (7) cyano;
  (8) nitro;
  (9) -$Z_4$-$NR_7R_8$;
  (10) -$Z_4$-$N(R_9)$-$Z_5$-$NR_{10}R_{11}$;
  (11) -$Z_4$-$N(R_{12})$-$Z_5$-$R_6$;
  (12) —$P(O)(OR_6)_2$;
$R_2$ is hydrogen, $R_6$, -$Z_4$-$R_6$, or -$Z_{13}$-$NR_7R_8$;
$R_3$ is -$Z_4$-$R_6$ wherein $Z_4$ is a single bond and $R_6$ is heteroaryl which is unsubstituted or substituted with $Z_1$, $Z_2$ and one or more groups $Z_3$
$R_4$ and $R_5$ are each independently
  (1) hydrogen or $R_6$;
  (2) -$Z_4$-$N(R_9)$-$Z_5$-$NR_{10}R_{11}$;
  (3) —$N(R_9)Z_4R_6$; or
  (4) together with the nitrogen atom to which they are attached complete a 3- to 8-membered saturated or unsaturated heterocyclic ring which is unsubstituted or substituted with $Z_1$, $Z_2$ and $Z_3$, which heterocyclic ring may optionally have fused to it a benzene ring itself unsubstituted or substituted with $Z_1$, $Z_2$ and $Z_3$;
$R_7$, $R_8$, $R_9$, $R_{10}$, $R_{11}$ and $R_{12}$
  (1) are each independently hydrogen or $R_6$
  (2) $R_7$ and $R_8$ may together be alkylene, alkenylene or heteroalkyl, completing a 3- to 8-membered saturated or unsaturated ring with the nitrogen atom to which they are attached, which ring is unsubstituted or substituted with $Z_1$, $Z_2$ and $Z_3$; or
  (3) any two of $R_9$, $R_{10}$ and $R_{11}$, may together be alkylene or alkenylene completing a 3- to 8-membered saturated or unsaturated ring together with the nitrogen atoms to which they are attached, which ring is unsubstituted or substituted with $Z_1$, $Z_2$ and $Z_3$;
$R_{13}$ is
  (1) cyano;
  (2) nitro;
  (3) —$NH_2$;
  (4) —NHOalkyl;
  (5) —OH;
  (6) —NHOaryl;
  (7) —NHCOOalkyl;
  (8) —NHCOOaryl;
  (9) —$NHSO_2$alkyl;
  (10) —$NHSO_2$aryl;
  (11) aryl;
  (12) heteroaryl;
  (13) —Oalkyl; or
  (14) —Oaryl;
$R_{14}$ is
  (1) —$NO_2$;
  (2) —COOalkyl; or
  (3) —COOaryl;
$R_{15}$ is
  (1) hydrogen;
  (2) alkyl;
  (3) aryl;
  (4) arylalkyl; or
  (5) cycloalkyl;
$Z_1$, $Z_2$ and $Z_3$ are each independently
  (1) hydrogen or $Z_6$, where $Z_6$ is (i) alkyl, alkenyl, alkynyl, cycloalkyl, cycloalkylalkyl, cycloalkenyl, cycloalkenylalkyl, aryl, aralkyl, alkylaryl, cycloalkylaryl, heterocyclo, or heterocycloalkyl; (ii) a group (i) which is itself substituted by one or more of the same or different groups (i); or (iii) a group (i) or (ii) which is substituted by one or more of the following groups (2) to (16) of the definition of $Z_1$, $Z_2$ and $Z_3$;
  (2) —OH or —$OZ_6$;
  (3) —SH or —$SZ_6$;
  (4) —$C(O)_qH$, —$C(O)_qZ_6$, or —O—$C(O)_qZ_6$;
  (5) —$SO_3H$, —$S(O)_qZ_6$; or $S(O)_qN(Z_9)Z_6$;
  (6) halo,
  (7) cyano;
  (8) nitro;
  (9) -$Z_4$-$NZ_7Z_8$;
  (10) -$Z_4$-$N(Z_9)$-$Z_5$-$NZ_7Z_8$;
  (11) -$Z_4$-$N(Z_{10})$-$Z_5$-$Z_6$;
  (12) -$Z_4$-$N(Z_{10})$-$Z_5$-H;
  (13) oxo;
  (14) —O—$C(O)$-$Z_6$;
  (15) any two of $Z_1$, $Z_2$, and $Z_3$ may together be alkylene or alkenylene completing a 3- to 8-membered saturated or unsaturated ring together with the atoms to which they are attached; or
  (16) any two of $Z_1$, $Z_2$, and $Z_3$ may together be —O—$(CH_2)_r$—O— where r is 1 to 5, completing a 4- to 8-membered ring together with the atoms to which they are attached,
$Z_4$ and $Z_5$ are each independently
  (1) a single bond;
  (2) -$Z_{11}$-$S(O)_q$-$Z_{12}$-;
  (3) -$Z_{11}$-$C(O)$-$Z_{12}$-;
  (4) -$Z_{11}$-$C(S)$-$Z_{12}$-;
  (5) -$Z_{11}$-O-$Z_{12}$-;
  (6) -$Z_{11}$-S-$Z_{12}$-;
  (7) -$Z_{11}$-O—$C(O)$-$Z_{12}$-; or
  (8) -$Z_{11}$-$C(O)$—O-$Z_{12}$-;
$Z_7$, $Z_8$, $Z_9$ and $Z_{10}$
  (1) are each independently hydrogen or $Z_6$;
  (2) $Z_7$ and $Z_8$, or $Z_6$ and $Z_{10}$, may together be alkylene or alkenylene, completing a 3- to 8-membered saturated or unsaturated ring together with the atoms to which they are attached, which ring is unsubstituted or substituted with $Z_1$, $Z_2$ and $Z_3$; or (3) $Z_7$ or $Z_8$, together with $Z_9$, may be alkylene or alkenylene completing a 3- to 8-membered saturated or unsaturated ring together with the nitrogen atoms to which they are attached, which ring is unsubstituted or substituted with $Z_1$, $Z_2$ and $Z_3$;

$Z_{11}$ and $Z_{12}$ are each independently
(1) a single bond;
(2) alkylene;
(3) alkenylene; or
(4) alkynylene; and $Z_{13}$ is
(1) a single bond;
(2) -$Z_{11}$-S(O)$_q$-$Z_{12}$-;
(3) -$Z_{11}$-C(O)-$Z_{12}$-;
(4) -$Z_{11}$-C(S)-$Z_{12}$-;
(5) -$Z_{11}$-O-$Z_{12}$-;
(6) -$Z_{11}$-O-$Z_{12}$-;
(7) -$Z_{11}$-O—C(O)-$Z_{12}$-;
(8) -$Z_{11}$-C(O)—O-$Z_{12}$-;
(9) —C(NR$_{13}$)—;
(10) —C(CHR$_{14}$)—; or
(11) —C(C(R$_{14}$)$_2$)—;

provided said compound is other than a compound of formula (vii)

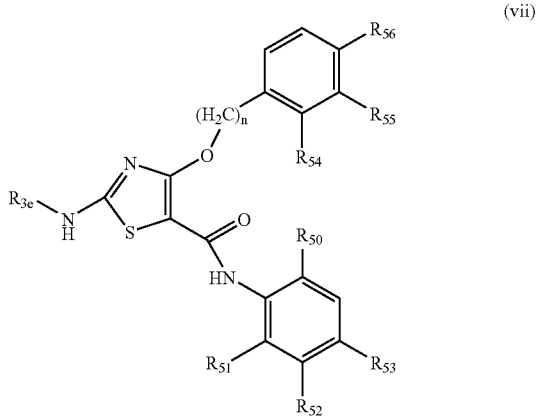

where
$R_{3e}$ is pyridyl or pryimidinyl optionally substituted with halogen or alkyl;
$R_{50}$ and $R_{51}$ are each independently hydrogen, halogen or alkyl;
$R_{52}$ and $R_{53}$ are each independently hydrogen, halogen, alkyl or haloalkyl;
$R_{54}$ and $R_{56}$ are each independently hydrogen, halogen, alkyl, nitro or amino;
$R_{55}$ is hydrogen, halogen, alkyl, haloalkyl, alkoxy, haloalkoxy, alkylthio, haloalkylthio, or alkoxycarbonyl; and
n is zero or 1.

In another embodiment, the present invention is directed to a method for the treatment of proliferative diseases, comprising the compound of formula I wherein $R_1$ is hydrogen, halo, alkyl, aryl, alkoxy, alkoxycarbonyl, or aryloxycarbonyl.

In another embodiment, the present invention is directed to a method for the treatment of proliferative diseases, comprising the compound of formula I wherein $R_1$ is hydrogen.

In another embodiment, the present invention is directed to a method for the treatment of proliferative diseases, comprising the compound of formula I wherein $R_2$ is hydrogen.

In another embodiment, the present invention is directed to a method for the treatment of proliferative diseases, comprising the compound of formula I wherein $R_4$ is hydrogen.

In another embodiment, the present invention is directed to a method for the treatment of proliferative diseases, comprising the compound of formula I wherein $R_5$ is an aryl group which is substituted with $Z_1$, $Z_2$ and one or more groups $Z_3$.

In another embodiment, the present invention is directed to a method for the treatment of proliferative diseases, comprising the compound of formula I wherein $R_1$ is hydrogen or alkyl, $R_2$ and $R_4$ are independently hydrogen or alkyl, and $R_5$ is aryl which is unsubstituted or substituted with $Z_1$, $Z_2$ and one or more groups $Z_3$.

In another embodiment, the present invention is directed to a method for the treatment of proliferative diseases, comprising the compound of formula I wherein $R_5$ is aryl which is unsubstituted or independently substituted with one or more alkyl or halo.

In another embodiment, the present invention is directed to a method for the treatment of proliferative diseases, comprising the compound of formula I wherein $R_3$ is heteroaryl substituted optionally substituted with $Z_1$ and $Z_2$ and substituted with at least one group $Z_3$ where $Z_3$ is $Z_6$.

In another embodiment, the present invention is directed to a method for the treatment of proliferative diseases, comprising the compound of formula I wherein $Z_6$ is heterocyclo optionally substituted with one or more hydroxyalkyl.

In another embodiment, the present invention is directed to a use of the compound of formula I which comprises a synergistically, therapeutically effective amount of (1) at least one anti-proliferative agent(s) and 2) a compound of formula I.

In another embodiment, the invention is directed to a method for the treatment of proliferative diseases, wherein the anti-proliferative agent is selected from the group consisting of selected from the group consisting of an anthracycline drug, a vinca drug, a mitomycin, a bleomycin, a cytotoxic nucleoside, a taxane, an epothilone, discodermolide, a pteridine drug, a diynene, an aromatase inhibitor and a podophyllotoxin.

In another embodiment, the invention is directed to a method for the treatment of proliferative diseases, wherein the anti-proliferative agent is selected from carboplatin, doxorubicin, and CPT-11.

In another embodiment, the invention is directed to a pharmaceutical composition for the treatment of cancer which comprises a synergistic combination of at least one anti-proliferative agent and a compound of formula I, and a pharmaceutically acceptable carrier.

In another embodiment, the invention is directed to a pharmaceutical composition wherein the antiproliferative agent is one or more agent selected from the group consisting of a microtubule-stabilizing agent, a microtubule-disruptor agent, an alkylating agent, an anti-metabolite, epidophyllotoxin, an antineoplastic enzyme, a topoisomerase inhibitor, procarbazine, mitoxantrone, inhibitors of cell cycle progression, a platinum coordination complex, an anthracycline drug, a vinca drug, CDK inhibitors, a mitomycin, a bleomycin, a cytotoxic nucleoside, a taxane, an epothilone, discodermolide, a pteridine drug, a diynene, an aromatase inhibitor and a podophyllotoxin.

The terms "alk" or "alkyl" refer to straight or branched chain hydrocarbon groups having 1 to 12 carbon atoms, or 1 to 8 carbon atoms. The expression "lower alkyl", refers to alkyl groups of 1 to 4 carbon atoms.

The term "alkenyl" refers to straight or branched chain hydrocarbon groups of 2 to 10, or 2 to 4, carbon atoms having at least one double bond. Where an alkenyl group is bonded to a nitrogen atom, it is preferred that such group not be bonded directly through a carbon bearing a double bond.

The term "alkynyl" refers to straight or branched chain hydrocarbon groups of 2 to 10, or 2 to 4, carbon atoms having at least one triple bond. Where an alkynyl group is bonded to a nitrogen atom, it is preferred that such group not be bonded directly through a carbon bearing a triple bond.

The term "alkylene" refers to a straight chain bridge of 1 to 5 carbon atoms connected by single bonds (e.g., —$(CH_2)_x$— wherein x is 1 to 5), which may be substituted with 1 to 3 lower alkyl groups.

The term "alkenylene" refers to a straight chain bridge of 2 to 5 carbon atoms having one or two double bonds that is connected by single bonds and may be substituted with 1 to 3 lower alkyl groups. Exemplary alkenylene groups are —CH=CH—CH=CH—, —$CH_2$—CH=CH—, —$CH_2$—CH=CH—$CH_2$—, —$C(CH_3)_2$CH=CH— and —CH($C_2H_5$)—CH=CH—.

The term "alkynylene" refers to a straight chain bridge of 2 to 5 carbon atoms that has a triple bond therein, is connected by single bonds, and may be substituted with 1 to 3 lower alkyl groups. Exemplary alkynylene groups are —C≡C—, —$CH_2$—C≡C—, —CH($CH_3$)—C≡C— and —C≡C—CH($C_2H_5$)$CH_2$—.

The terms "ar" or "aryl" refer to aromatic cyclic groups (for example 6 membered monocyclic, 10 membered bicyclic or 14 membered tricyclic ring systems) which contain 6 to 14 carbon atoms. Exemplary aryl groups include phenyl, naphthyl, biphenyl and anthracene.

The terms "cycloalkyl" and "cycloalkenyl" refer to cyclic hydrocarbon groups of 3 to 12 carbon atoms.

The terms "halogen" and "halo" refer to fluorine, chlorine, bromine and iodine.

The term "unsaturated ring" includes partially unsaturated and aromatic rings.

The terms "heterocycle", "heterocyclic" or "heterocyclo" refer to fully saturated or unsaturated, including aromatic (i.e. "heteroaryl") cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclo groups include benzothiazolyl, benzoxazolyl, benzothienyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b] pyridinyl or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

The term "heteroaryl" refers to aromatic heterocyclic groups.

Exemplary heteroaryl groups include pyrrolyl, pyrazolyl, imidazolyl, oxazolyl, isoxazolyl, thiazolyl, thiadiazolyl, isothiazolyl, furyl, thienyl, oxadiazolyl, pyridinyl, pyrazinyl, pyrimidinyl, pyridazinyl, triazolyl, triazinyl, and the like.

Where q is 1 or 2, "—$C(O)_qH$" denotes —C(O)—H or —C(O)—OH; "—$C(O)_qR_6$" or "—$C(O)_qZ_6$" denote, respectively, —C(O)—$R_6$ or —C(O)$OR_6$, or —C(O)-$Z_6$ or —C(O)—$OZ_6$; "—O—$C(O)_qR_6$" or "—O—$C(O)_qZ_6$" denote, respectively, —O—C(O)—$R_6$ or —O—C(O)—$OR_6$, or —O—C(O)-$Z_6$ or —O—C(O)—$OZ_6$; and "$S(O)_qR_6$" or "—$S(O)_qZ_6$" denote, respectively, —SO—$R_6$ or —$SO_2$—$R_6$, or —SO-$Z_6$ or —$SO_2$-$Z_6$.

When a group is referred to as being optionally substituted, it may be substituted with one to five, or with one to three, substituents such as F, Cl, Br, I, trifluoromethyl, trifluoromethoxy, hydroxy, lower alkoxy, cycloalkoxy, heterocyclooxy, oxo, lower alkanoyl, aryloxy, lower alkanoyloxy, amino, lower alkylamino, arylamino, aralkylamino, cycloalkylamino, heterocycloamino, disubstituted amines in which the two amino substituents independently are selected from lower alkyl, aryl or aralkyl, lower alkanoylamino, aroylamino, aralkanoylamino, substituted lower alkanoylamino, substituted arylamino, substituted aralkylanoylamino, thiol, lower alkylthio, arylthio, aralkylthio, cycloalkylthio, heterocyclothio, lower alkylthiono, arylthiono, aralkylthiono, lower alkylsultonyl, arylsulfonyl, aralkylsulfonyl, sulfonamide (e.g., $SO_2NH_2$), substituted sulfonamide, nitro, cyano, carboxy, carbamyl (e.g., $CONH_2$), substituted carbamyl (e.g., CONH-lower alkyl, CONH-aryl, CONH-aralkyl or cases where there are two substituents on the nitrogen independently selected from lower alkyl, aryl or aralkyl), lower alkoxycarbonyl, aryl, substituted aryl, guanidino, and heterocyclos (e.g., indolyl, imidazolyl, furyl, thienyl, thiazolyl, pyrrolidyl, pyridyl, pyrimidyl and the like). Where noted above that the substituent is further substituted, it will be substituted with F, Cl, Br, I, optionally substituted lower alkyl, hydroxy, optionally substituted lower alkoxy, optionally substituted aryl, or optionally substituted aralkyl.

All stereoisomers of the Formula I compounds of the instant invention are contemplated, either in admixture or in pure or substantially pure form. The definition of the formula I compounds embraces all possible stereoisomers and their mixtures. The Formula I definitions very particularly embrace the racemic forms and the isolated optical isomers having the specified activity.

Compounds of the formula I may in some cases form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts useful, although other salts are useful, for example, in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates, undecanoates, and the like.

Exemplary basic salts (formed, for example, where the R substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I may be hydrates.

All stereoisomers of the present compounds, such as those which may exist due to asymmetric carbons on the R substituents of the compound of the formula I, including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

Throughout the specification, groups and substituents thereof are chosen to provide stable moieties and compounds.

The combination of compounds is a synergistic combination. Synergy, as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect may be clearly demonstrated at suboptimal concentrations of the compounds. Synergy can be in terms of lower cytotoxicity, increased efficacy, or some other beneficial effect of the combination compared with the individual components.

"Therapeutically effective amount" is intended to include an amount of a compound of the present invention alone or an amount of the combination of compounds claimed or an amount of a compound of the present invention in combination with other active ingredients effective to treat the inflammatory diseases described herein.

A "synergistically, therapeutically effective amount" is a therapeutically effect amount which is provided by a synergistic combination.

A particular Src Kinase inihibitor for use in the methods of the invention is Compound 1: 'N-(2-Chloro-6-methylphenyl)-2-[[6-[4-(2-hydroxyethyl)-1-piperazinyl]-2-methyl-4-pyrimidinyl]amino]-5-thiazolecarboxamide, the compound is also known as N-(2-Chloro-6-methylphenyl)-2-[[6-[4-(2-hydroxyethyl)-1-piperazinyl]-2-methyl-4-pyrimidinyl]amino]-5-thiazolecarboxamide.

Compound 1, an exemplary Src Kinase inhibitor of the invention, competes with ATP for the ATP-binding site in the kinase domain of selected protein tyrosine kinases (PTKs), potently inhibits the Src family kinases (SFKs, including: Fyn, Yes, Yrk, Blk, Fgr, Hck, Lyn, and Frk subfamily members Frk/Rak and Iyk/Bsk).

In another embodiment of the invention a compound of Formulas I is administered in conjunction with at least one anti-neoplastic agent.

As used herein, the phrase "anti-neoplastic agent" is synonymous with "chemotherapeutic agent" and/or "anti-proliferative agent" and refers to compounds that prevent cancer, or hyperproliferative cells from multiplying. Anti-proliferative agents prevent cancer cells from multiplying by: (1) interfering with the cell's ability to replicate DNA and (2) inducing cell death and/or apoptosis in the cancer cells.

Classes of compounds that may be used as anti-proliferative cytotoxic agents and/or anti-proliferative agents include the following:

Alkylating agents (including, without limitation, nitrogen mustards, ethylenimine derivatives, alkyl sulfonates, nitrosoureas and triazenes): Uracil mustard, Chlormethine, Cyclophosphamide (Cytoxan@), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as Taxol®), Mithramycin, Deoxyco-formycin, Mitomycin-C, L Asparaginase, Interferons (especially IFN-a), Etoposide, and Teniposide.

Other anti-proliferative cytotoxic agents and/or anti-proliferative agents are navelbene, CPT-11, anastrazole, letrazole, capecitabine, reloxafine, cyclophosphamide, ifosamide, and droloxafine.

The phrase "radiation therapy" includes, but is not limited to, x-rays or gamma rays which are delivered from either an externally applied source such as a beam or by implantation of small radioactive sources.

Microtubule affecting agents interfere with cellular mitosis and are well known in the art for their anti-proliferative cytotoxic activity. Microtubule affecting agents useful in the invention include, but are not limited to, allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, epothilone C, epothilone D, desoxyepothilone A, desoxyepothilone B, [1S-[1R*,3R*(E), 7R*,10S*,11R*,12R*,16S*]]-7-11-dihydroxy-8,8,10,12, 16-pentamethyl-3-[1-methyl-2-(2-methyl-4-thiazolyl) ethenyl]-4-aza-17oxabicyclo[14.1.0]heptadecane-5,9-dione (disclosed in U.S. Pat. No. 6,262,094, issued Jul. 17, 2001), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17dioxabicyclo[14.1.0]-heptadecane-5,9-dione (disclosed in U.S. Ser. No. 09/506, 481 filed on Feb. 17, 2000, and examples 7 and 8 herein), [1S-1R*,3R*(E),7R*,10S*,11R*,12R*, 16S*]]-7,11-dihydroxy-8,8,10,12,16-pentamethyl-3-[1-methyl-2-(2-methyl-4-thiazolyl)ethenyl]-4-aza-17oxabicyclo[14.1.0]-heptadecane-5,9-dione, [1S-[1R*,3R*(E),7R*,10S*,11R*,12R*, 16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione, and derivatives thereof; and other microtubule-disruptor agents. Additional antineoplastic agents include, discodermolide (see Service, (1996) Science, 274:2009) estramustine, nocodazole, MAP4, and the like. Examples of such agents are also described in the scientific and patent literature, see, e.g., Bulinski (1997) *J. Cell Sci.* 110:3055 3064; Panda (1997) *Proc. Natl. Acad. Sci. USA* 94:10560-10564; Muhlradt (1997) Cancer Res. 57:3344-3346; Nicolaou (1997) *Nature* 387:268-272; Vasquez (1997) *Mol. Biol. Cell.* 8:973-985; Panda (1996) *J. Biol. Chem.* 271:29807-29812.

In cases where it is desirable to render aberrantly proliferative cells quiescent in conjunction with or prior to treatment with the chemotherapeutic methods of the invention, hormones and steroids (including synthetic analogs): 17a-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, hlorotrianisene, Hydroxyprogesterone, Aminoglutethimide, Estramustine, Medroxyprogesteroneacetate, Leuprolide, Flutamide, Toremifene, Zoladex can also be administered to the patient.

Also suitable for use in the combination chemotherapeutic methods of the invention are antiangiogenics such as matrix metalloproteinase inhibitors, and other VEGF inhibitors, such as anti-VEGF antibodies and small molecules such as ZD6474 and SU6668 are also included. Anti-Her2 antibodies from Genetech may also be utilized. A suitable EGFR inhibitor is EKB-569 (an irreversible inhibitor). Also included are Imclone antibody C225 immunospecific for the EGFR, and src inhibitors.

Also suitable for use as an antiproliferative cytostatic agent is Casodex™ which renders androgen-dependent carcinomas non-proliferative. Yet another example of a cytostatic agent is the antiestrogen Tamoxifen which inhibits the proliferation or growth of estrogen dependent breast cancer. Inhibitors of the transduction of cellular proliferative signals are cytostatic agents. Examples are epidermal growth factor inhibitors, Her-2 inhibitors, MEK-1 kinase inhibitors, MAPK kinase inhibitors, PI3 inhibitors, Src kinase inhibitors, and PDGF inhibitors.

As mentioned, certain anti-proliferative agents are anti-angiogenic and antivascular agents and, by interrupting blood flow to solid tumors, render cancer cells quiescent by depriving them of nutrition. Castration, which also renders androgen dependent carcinomas non-proliferative, may also be utilized. Starvation by means other than surgical disruption of blood flow is another example of a cytostatic agent. A particular class of antivascular cytostatic agents is the combretastatins. Other exemplary cytostatic agents include MET kinase inhibitors, MAP kinase inhibitors, inhibitors of non-receptor and receptor tyrosine kinases, inhibitors of integrin signaling, and inhibitors of insulin-like growth factor receptors.

Also suitable are anthracyclines (e.g., daunorubicin, doxorubicin), cytarabine (ara-C; Cytosar-U®); 6-thioguanine (Tabloid®), mitoxantrone (Novantrone®) and etoposide (Ve-Pesid®), amsacrine (AMSA), and all-trans retinoic acid (ATRA).

Thus, the present invention provides methods for the synergistic treatment of a variety of cancers, including, but not limited to, the following:

carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma);

hematopoietic tumors of lymphoid lineage including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, histiocytic lymphoma, and Burketts lymphoma;

hematopoietic tumors of myeloid lineage including acute and chronic myelogenous leukemias, myelodysplastic syndrome, myeloid leukemia, and promyelocytic leukemia;

tumors of the central and peripheral nervous system including astrocytoma, neuroblastoma, glioma, and schwannomas;

tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

The present invention provides methods for the synergistic treatment of a variety of non-cancerous proliferative diseases. The invention is used to treat GIST, Breast cancer, pancreatic cancer, colon cancer, NSCLC, CML, and ALL, sarcoma, and various pediatric cancers.

The compounds of the present invention are useful for the treatment of cancers such as chronic myelogenous leukemia (CML), gastrointestinal stromal tumor (GIST), small cell lung cancer (SCLC), non-small cell lung cancer (NSCLC), ovarian cancer, melanoma, mastocytosis, germ cell tumors, acute myelogenous leukemia (AML), pediatric sarcomas, breast cancer, colorectal cancer, pancreatic cancer, prostate cancer and others known to be associated with protein tyrosine kinases such as, for example, SRC, BCR-ABL and c-KIT. The compounds of the present invention are also useful in the treatment of cancers that are sensitive to and resistant to chemotherapeutic agents that target BCR-ABL and c-KIT, such as, for example, Gleevec® (STI-571).

In another embodiment of this invention, a method is provided for the synergistic treatment of cancerous tumors. Advantageously, the synergistic method of this invention reduces the development of tumors, reduces tumor burden, or produces tumor regression in a mammalian host.

Methods for the safe and effective administration of most of these chemotherapeutic agents are known to those skilled in the art. In addition, their administration is described in the standard literature.

For example, the administration of many of the chemotherapeutic agents is described in the "Physicians' Desk Reference" (PDR), e.g., 1996 edition (Medical Economics Company, Montvale, N.J. 07645-1742, USA); the disclosure of which is incorporated herein by reference thereto.

A compound of Formula I for use in the methods of the present invention include: 'N-(2-Chloro-6-methylphenyl)-2-[[6-[4-(2-hydroxyethyl)-1-piperazinyl]-2-methyl-4-pyrimidinyl]amino]-5-thiazolecarboxamide; and pharmaceutically acceptable salts, solvates and hydrates thereof.

The compounds of Formula I may be prepared by the procedures described in PCT publication, WO 00/62778 published Oct. 26, 2000.

The present invention also encompasses a pharmaceutical composition useful in the treatment of cancer, comprising the administration of a therapeutically effective amount of the combinations of this invention, with or without pharmaceutically acceptable carriers or diluents. The synergistic pharmaceutical compositions of this invention comprise an antiproliferative agent or agents, a formula I compound, and a pharmaceutically acceptable carrier. The methods entail the use of a neoplastic agent in combination with a Formula I compound. The compositions of the present invention may further comprise one or more pharmaceutically acceptable additional ingredient(s) such as alum, stabilizers, antimicrobial agents, buffers, coloring agents, flavoring agents, adjuvants, and the like. The antineoplastic agents, Formula I, compounds and compositions of the present invention may be administered orally or parenterally including the intravenous, intramuscular, intraperitoneal, subcutaneous, rectal and topical routes of administration.

For oral use, the antineoplastic agents, Formula I compounds and compositions of this invention may be administered, for example, in the form of tablets or capsules, powders, dispersible granules, or cachets, or as aqueous solutions or suspensions. In the case of tablets for oral use, carriers which are commonly used include lactose, corn starch, magnesium carbonate, talc, and sugar, and lubricating agents such as magnesium stearate are commonly added. For oral administration in capsule form, useful carriers include lactose, corn starch, magnesium carbonate, talc, and sugar. When aqueous suspensions are used for oral administration, emulsifying and/or suspending agents are commonly added.

In addition, sweetening and/or flavoring agents may be added to the oral compositions. For intramuscular, intraperitoneal, subcutaneous and intravenous use, sterile solutions of the active ingredient(s) are usually employed, and the pH of the solutions should be suitably adjusted and buffered. For intravenous use, the total concentration of the solute(s) should be controlled in order to render the preparation isotonic.

For preparing suppositories according to the invention, a low melting wax such as a mixture of fatty acid glycerides or cocoa butter is first melted, and the active ingredient is dispersed homogeneously in the wax, for example by stirring. The molten homogeneous mixture is then poured into conveniently sized molds and allowed to cool and thereby solidify.

Liquid preparations include solutions, suspensions and emulsions. Such preparations are exemplified by water or water/propylene glycol solutions for parenteral injection. Liquid preparations may also include solutions for intranasal administration.

Aerosol preparations suitable for inhalation may include solutions and solids in powder form, which may be in combination with a pharmaceutically acceptable carrier, such as an inert compressed gas.

Also included are solid preparations which are intended for conversion, shortly before use, to liquid preparations for either oral or parenteral administration. Such liquid forms include solutions, suspensions and emulsions.

The compounds of Formula I, as well as the anti-neoplastic agents, described herein may also be delivered transdermally. The transdermal compositions can take the form of creams, lotions, aerosols and/or emulsions and can be included in a transdermal patch of the matrix or reservoir type as are conventional in the art for this purpose.

The combinations of the present invention may also be used in conjunction with other well known therapies that are selected for their particular usefulness against the condition that is being treated.

If formulated as a fixed dose, the active ingredients of the combination compositions of this invention are employed within the dosage ranges described below. Alternatively, the anti-neoplastic, and Formula I compounds may be administered separately in the dosage ranges described below. In another embodiment of the present invention, the antineoplastic agent is administered in the dosage range described below following or simultaneously with administration of the Formula I compound in the dosage range described below.

Table 1 sets forth chemotherapeutic combinations and exemplary dosages for use in the methods of the present invention. Where "Compound of Formula I" appears, any of the variations of Formula I set forth herein are contemplated for use in the chemotherapeutic combinations.

TABLE 1

| CHEMOTHERAPEUTIC COMBINATION | DOSAGE mg/m$^2$ (per dose) |
|---|---|
| Compound of Formula I | 0.1-100 mg/m2 |
| + Cisplatin | 5-150 mg/m2 |
| Compound of Formula I | 0.1-100 mg/m2 |
| + Carboplatin | 5-1000 mg/m2 |
| Compound of Formula I | 0.1-100 mg/m2 |
| + Radiation | 200-8000 cGy |
| Compound of Formula I | 0.1-100 mg/m2 |
| + CPT-11 | 5-400 mg/m2 |
| Compound of Formula I | 0.1-100 mg/m2 |
| + Paclitaxel | 40-250 mg/m2 |
| Compound of Formula I | 0.1-100 mg/m2 |
| + Paclitaxel | 40-250 mg/m2 |
| + Carboplatin | 5-1000 mg/m2 |
| Compound of Formula I | 0.1-100 mg/m2 |
| + 5FU and optionally | 5-5000 mg/m2 |
| + Leucovorin | 5-1000 mg/m2 |
| Compound of Formula I | 0.1-100 mg/m2 |
| + Epothilone | 1-500 mg/m2 |
| Compound of Formula I | 0.1-100 mg/m2 |
| + Gemcitabine | 100-3000 mg/m2 |
| Compound of Formula I | 0.1-100 mg/m2 |
| + UFT and optionally | 50-800 mg/m2 |

TABLE 1-continued

| CHEMOTHERAPEUTIC COMBINATION | DOSAGE mg/m² (per dose) |
|---|---|
| + leucovorin | 5-1000 mg/m2 |
| Compound of Formula I | 0.1-100 mg/m2 |
| + Gemcitabine | 100-3000 mg/m2 |
| + Cisplatin | 5-150 mg/m2 |
| Compound of Formula I | 0.1-100 mg/m2 |
| + UFT | 50-800 mg/m2 |
| +Leucovorin | 5-1000 mg/m2 |
| Compound of Formula I | 0.1-100 mg/m2 |
| + Cisplatin | 5-150 mg/m2 |
| + paclitaxel | 40-250 mg/m2 |
| Compound of Formula I | 0.1-100 mg/m2 |
| + Cisplatin | 5-150 mg/m2 |
| + 5FU | 5-5000 mg/m2 |
| Compound of Formula I | 0.1-100 mg/m2 |
| + Oxaliplatin | 5-200 mg/m2 |
| + CPT-11 | 4-400 mg/m2 |
| Compound of Formula I | 0.1-100 mg/m2 |
| + 5FU | 5-5000 mg/m2 |
| + CPT-11 and optionally | 4-400 mg/m2 |
| + leucovorin | 5-1000 mg/m2 |
| Compound of Formula I | 0.1-100 mg/m2 |
| + 5FU | 5-5000 mg/m2 |
| + radiation | 200-8000 cGy |
| Compound of Formula I | 0.1-100 mg/m2 |
| + radiation | 200-8000 cGy |
| + 5FU | 5-5000 mg/m2 |
| + Cisplatin | 5-150 mg/m2 |
| Compound of Formula I | 0.1-100 mg/m2 |
| + Oxaliplatin | 5-200 mg/m2 |
| + 5FU and optionally | 5-5000 mg/m2 |
| + Leucovorin | 5-1000 mg/m2 |
| Compound of Formula I | 0.1-100 mg/m2 |
| + paclitaxel | 40-250 mg/m2 |
| + CPT-11 | 4-400 mg/m2 |
| Compound of Formula I | 0.1-100 mg/m2 |
| + paclitaxel | 40-250 mg/m2 |
| + 5-FU | 5-5000 mg/m2 |
| Compound of Formula I | 0.1-100 mg/m2 |
| + UFT | 50-800 mg/m2 |
| + CPT-11 and optionally | 4-400 mg/m2 |
| + leucovorin | 5-1000 mg/m2 |

In the above Table 1, "5FU" denotes 5-fluorouracil, "Leucovorin" can be employed as leucovorin calcium, "UFT" is a 1:4 molar ratio of tegafur:uracil, and "Epothilone" is a compound described in WO 99/02514 or WO 00/50423, both incorporated by reference herein in their entirety.

While Table 1 provides exemplary dosage ranges of the Formula I compounds and certain anticancer agents of the invention, when formulating the pharmaceutical compositions of the invention the clinician may utilize dosages as warranted by the condition of the patient being treated. For example, Compound 1 may be administered at 25-60 mg/m2 every 3 weeks. Compound 2, may be administered at a dosage ranging from 25-500 mg/m2 every three weeks for as long as treatment is required. Dosages for cisplatin are 75-120 mg/m2 administered every three weeks. Dosages for carboplatin are within the range of 200-600 mg/m2 or an AUC of 0.5-8 mg/ml×min; or an AUC of 4-6 mg/ml×min. When the method employed utilizes radiation, dosages are within the range of 200-6000 cGY. Dosages for CPT-11 are within 100-125 mg/m2, once a week. Dosages for paclitaxel are 130-225 mg/m2 every 21 days. Dosages for gemcitabine are within the range of 80-1500 mg/m2 administered weekly. UFT is used within a range of 300-400 mg/m2 per day when combined with leucovorin administration. Dosages for leucovorin are 10-600 mg/m2 administered weekly.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. Intermittent therapy (e.g., one week out of three weeks or three out of four weeks) may also be used.

Certain cancers can be treated effectively with compounds of Formula I and a plurality of anticancer agents. Such triple and quadruple combinations can provide greater efficacy. When used in such triple and quadruple combinations the dosages set forth above can be utilized. Other such combinations in the above Table I can therefore include "Compound 1" in combination with (1) mitoxantrone+prednisone; (2) doxorubicin+carboplatin; or (3 herceptin+tamoxifen. 5-FU can be replaced by UFT in any of the above combinations.

When employing the methods or compositions of the present invention, other agents used in the modulation of tumor growth or metastasis in a clinical setting, such as antiemetics, can also be administered as desired.

The present invention encompasses a method for the synergistic treatment of cancer wherein a neoplastic agent and a Formula I compound are administered simultaneously or sequentially. Thus, while a pharmaceutical formulation comprising antineoplastic agent(s) and a Formula I compound may be advantageous for administering the combination for one particular treatment, prior administration of the antineoplastic agent(s) may be advantageous in another treatment. It is also understood that the instant combination of antineoplastic agent(s) and Formula I compound may be used in conjunction with other methods of treating cancer (such as cancerous tumors) including, but not limited to, radiation therapy and surgery. It is further understood that a cytostatic or quiescent agent, if any, may be administered sequentially or simultaneously with any or all of the other synergistic therapies. It is further understood that the routes of administration may vary between the compounds of Formula I and the antineoplastic.

The combinations of the instant invention may also be co-administered with other well known therapeutic agents that are selected for their particular usefulness against the condition that is being treated. Combinations of the instant invention may alternatively be used sequentially with known pharmaceutically acceptable agent(s) when a multiple combination formulation is inappropriate.

The chemotherapeutic agent(s) and/or radiation therapy can be administered according to therapeutic protocols well known in the art. It will be apparent to those skilled in the art that the administration of the chemotherapeutic agent(s) and/or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent(s) or radiation) on the patient, and in view of the observed responses of the disease to the administered therapeutic agents.

In the methods of this invention, a compound of Formula I is administered simultaneously or sequentially with an antiproliferative agent and/or radiation. Thus, it is not necessary that the chemotherapeutic agent(s) and compound of Formula I, or the radiation and the compound of Formula I, be administered simultaneously or essentially simultaneously. The advantage of a simultaneous or essentially simultaneous administration is well within the determination of the skilled clinician.

Also, in general, the compound of Formula I, and chemotherapeutic agent(s) do not have to be administered in the same pharmaceutical composition, and may, because of different physical and chemical characteristics, have to be administered by different routes. For example, the compound of Formula I may be administered orally to generate and maintain good blood levels thereof, while the chemotherapeutic agent(s) may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of compound of Formula I and antiproliferative cytotoxic agent(s) or radiation will depend upon the diagnosis of the attending physicians and their judgment of the condition of the patient and the appropriate treatment protocol.

If the compound of Formula I and the anti-neoplastic agent(s) and/or radiation are not administered simultaneously or essentially simultaneously, then the initial order of administration of the compound of Formula I, and the chemotherapeutic agent(s) and/or radiation, may be varied. Thus, for example, the compound of Formula I may be administered first followed by the administration of the antiproliferative agent(s) and/or radiation; or the antiproliferative agent(s) and/or radiation may be administered first followed by the administration of the compound of Formula I. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the anti-neoplastic agent(s) and/or radiation may be administered initially, especially if a cytotoxic agent is employed. The treatment is then continued with the administration of the compound of Formula I and optionally followed by administration of a cytostatic agent, if desired, until the treatment protocol is complete.

Thus, in accordance with experience and knowledge, the practicing physician can modify each protocol for the administration of a component (therapeutic agent—i.e., compound of Formula I, anti-neoplastic agent(s), or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

In order to facilitate a further understanding of the invention, the following examples are presented primarily for the purpose of illustrating more specific details thereof. The scope of the invention should not be deemed limited by the examples, but to encompass the entire subject matter defined by the claims.

Experimental Protocol

Compounds:

The following designations are used to identify the test compounds throughout the examples:

Compound 1: 'N-(2-Chloro-6-methylphenyl)-2-[[6-[4-(2-hydroxyethyl)-1-piperazinyl]-2-methyl-4-pyrimidinyl]amino]-5-thiazolecarboxamide;

Chemicals and Solutions:

Unless specified, chemicals and solutions used for the maintenance of cell culture were obtained from GIBCO/BRL. Sterile tissue culture ware was obtained from Corning, N.Y. All other reagents were from Sigma or Fisher at the highest grade available.

Drug Administration:

For PO and IV administration to mice, the Src inhibitor was dissolved in a mixture of propylene glycol/water (50:50). The volume of all compounds administered was 0.01 ml/gm of mice.

In Vivo Antitumor Testing:

The human tumor xenografts were maintained in Balb/c nu/nu nude or scid mice (Harlan, Indianapolis). Tumors were propagated as subcutaneous transplants using tumor fragments obtained from donor mice.

The required number of animals needed to detect a meaningful response were pooled at the start of the experiment and each was given a subcutaneous implant of a tumor fragment (~50 mg) with a 13-gauge trocar. For treatment of early-stage tumors, the animals were again pooled before distribution to the various treatment and control groups. For treatment of animals with advanced-stage disease, tumors were allowed to grow to the pre-determined size window (tumors outside the range were excluded) and animals were evenly distributed to various treatment and control groups. Treatment of each animal was based on individual body weight. Treated animals were checked daily for treatment related toxicity/mortality. Each group of animals was weighed before the initiation of treatment (Wt1) and then again following the last treatment dose (Wt2). The difference in body weight (Wt2−Wt1) provides a measure of treatment-related toxicity. Tumor response was determined by measurement of tumors with a caliper twice a week, until the tumors reach a predetermined "target" size of 1 gm. Tumor weights (mg) were estimated from the formula:

$$\text{Tumor weight} = (\text{length} \times \text{width}2) \div 2$$

Antitumor activity was evaluated at the maximum tolerated dose (MTD) which is defined as the dose level immediately below which excessive toxicity (i.e. more than one death) occurred. The MTD was frequently equivalent to OD. When death occurs, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Tumor response end-point was expressed in terms of tumor growth delay (T−C value) and tumor growth inhibition (%

T/C). Tumor growth delay is defined as the difference in time (days) required for the treated tumors (T) to reach a predetermined target size compared to those of the control group (C). For this purpose tumor weight of a group is expressed as medium tumor weight (MTW).

To estimate tumor cell kill, the tumor volume doubling time was first calculated with the formula:

TVDT=Median time (days) for control tumor weight to reach target size–Median time (days) for control tumor weight to reach half the target size And, Log cell kill (Lck)=T–C÷(3.32×TVDT)

To estimate tumor growth inhibition, the MTW at the end of treatment is determined for the treated group (T) and the untreated control group (C). Inhibition is expressed as the ratio (%) of treated (T)/control (C).

Cures were also used to assess activity. A mouse was considered cured when no mass larger than 35 mg was present at the site of tumor implant after a number of days post-treatment had elapsed equivalent to >10 TVDTs in that experiment. Therapeutic results were reported at the optimal dose (OD) and results were not used if more than one death occurred in the treated group. A maximum tolerated dose (MTD), although often synonymous with the OD, is defined as a dose immediately below that causing unacceptable toxicity (i.e. more than one death), or in the absence of any deaths, was assumed when accompanied by >20% body weight loss. There were typically 8 mice per treatment and control groups.

Activity for cytotoxic agents is defined as the attainment of tumor growth delay equivalent to ~1 Lck or 3.32×TVDT. For cytostatic agents, activity is defined as attainment of growth inhibition ~50% T/C (MTW) at the end of the treatment period.

EXAMPLE 1

Figure 1A:
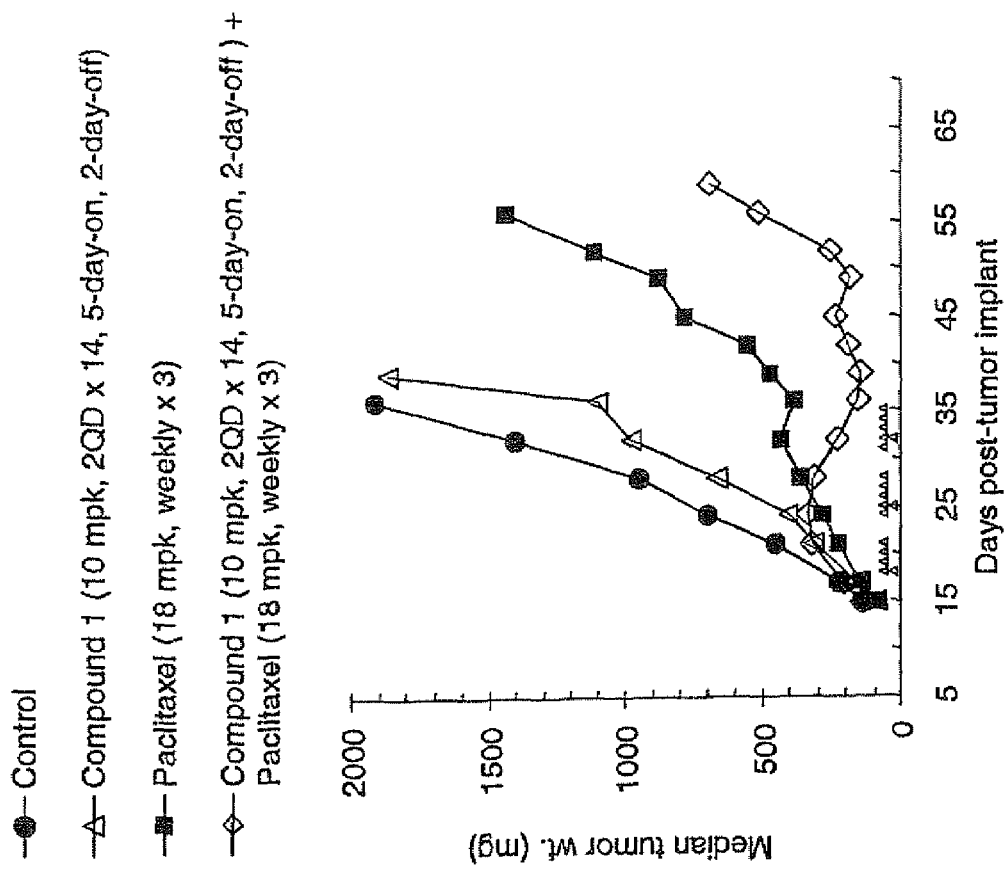

Synergistic Combination of Compound 1 with a Tubulin Interacting Antimitotic Agent (Exemplified by Paclitaxel) in the Treatment of Solid Malignancies In Vivo The combined antitumor effects of compound 1 and paclitaxel was evaluated in the PC3 human prostate carcinoma xenografts in nude mice. compound 1 was administered orally, twice-a-day, 5-day-on, 2-day-off, for a total of 14 days (2 qd×7). Paclitaxel was administered iv, weekly×3. Single agent compound 1 at a dose of 10 mpk produced a % T/C of 58% and growth delay (T−C) of 4.5 days (FIG. 1A). Single agent paclitaxel at a dose of 18 mpk elicited T−C of 22.5 days. The combined regimen produced antitumor effect that was more than additive of the individual effects of the single agent alone with a T-C of 37.2 days which was significantly better than the effects of either single agent alone (P=0.05). However, combination of the two agents in vitro produced only additive effect in a clonogenic cell survival assay (FIG. 1B). These results suggest that the in vivo synergistic interaction of compound 1 and paclitaxel may involve a mechanism that does not directly stem from the tumor cells themselves.

FIG. 1:

In FIG. 1A (A) Mice bearing the PC3 prostate carcinoma were treated when tumors reached ~100 mg. Compounds were administered as follows: compound 1 was administered orally (PO), twice-a-day for 14 days (2QD×14), with a 2 day break following every 5 days of treatment (5-day-on, 2-day-off). Paclitaxel was administered IV and was given weekly for 3 weeks. Treatment with both agents was begun on the same day, paclitaxel being given 1 hour after the first of two daily doses of compound 1. Each symbol represents the median tumor weight of a group of 8 mice. (B) PC3 cells in exponential growth phase were first exposed to compound 1 for 48 hr followed by paclitaxel for a further 16 hr. Cells were then washed and processed for colony formation assay. Line of additivity depicts the level of cytotoxicity if the two combined agents yield additive cytotoxicity and is the product of the surviving fractions of each agent given alone. Src family kinases play an important role in mitotic progression of cells from G2 to Mitotic (M) phases of the cell cycle, which may explain the synergistic interaction of Src inhibitors with antimitotic agents such as paclitaxel.

The present invention is not limited to the embodiments specifically described above, but is capable of variation and modification without departure from the scope of the appended claims.

What is claimed is:

1. A method for the treatment of cancer, which comprises administering to a mammalian specie in need thereof a synergistically, therapeutically effective amount of (1)[1S-[1R*, 3R*(E),7R*,10S*,11R*,12R*,16S*]]-7-11dihydroxy-8,8,10,12,16-pentamethyl-3-[1-methyl-2-(2-methyl-4-thiazolyl)ethenyl]-4-aza-17oxabicyclo[14.1.0]heptadecane-5,9-dione and (2) N-(2-chloro-6-methylphenyl)-2-[[6-[4-(2-hydroxyethyl)-1-piperazinyl]-2-methyl-4-pyrimidinyl]amino]-5-thiazolecarboxamide or pharmaceutically acceptable salt thereof, wherein the cancer is selected from prostate cancer or breast cancer.

2. The method according to claim 1 wherein [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17oxabicyclo[-14.1.0]heptadecane-5,9-dione is administered following administration of N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutical acceptable salt thereof.

3. The method according to claim 1, wherein [1S-[1R*,3R*(E),7R*,10S*,11R*,12R*,16S*]]7-11-dihydroxy-8,8,10,12,16-pentamethyl-3-[1-methyl-2-(2-methyl-4-thiazolyl)ethenyl]-4-aza-17oxabicyclo[14.1.0]heptadecane-5,9-dione is administered prior to the administration of N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt thereof.

4. The method according to claim 1 wherein [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17oxabicyclo[14.1.0]heptadecane-5,9-dione is administered simultaneously with N-(2-chloro-6-methylphenyl)-2-[[6-[4-(2-hydroxyethyl)-1-piperazinyl]-2-methyl-4-pyrimidinyl]amino]-5-thiazolecarboxamide or a pharmaceutically acceptable salt thereof.

5. The method according to claim 1 wherein the prostate or breast cancer is a refractory tumor.

6. The method of claim 1, wherein the cancer is prostate cancer.

7. The method of claim 1, wherein the cancer is breast cancer.

* * * * *

UNITED STATES PATENT AND TRADEMARK OFFICE
CERTIFICATE OF CORRECTION

| | | |
|---|---|---|
| PATENT NO. | : 7,622,472 B2 | Page 1 of 1 |
| APPLICATION NO. | : 12/047623 | |
| DATED | : November 24, 2009 | |
| INVENTOR(S) | : Francis Y. Lee | |

It is certified that error appears in the above-identified patent and that said Letters Patent is hereby corrected as shown below:

Claim 1:

Column 20, line 26, change "11dihydroxy" to -- 11-dihydroxy --.

Claim 2:

Column 20, line 37, change "[-14.1.0]" to -- [14.1.0] --.

Signed and Sealed this

Eighth Day of November, 2011

David J. Kappos
*Director of the United States Patent and Trademark Office*